(12) United States Patent
Grant et al.

(10) Patent No.: US 9,198,630 B2
(45) Date of Patent: Dec. 1, 2015

(54) METHOD AND COMPUTING UNIT FOR MEASURING AND DISPLAYING THE BONE DENSITY OF A PATIENT

(71) Applicants: SIEMENS AKTIENGESELLSCHAFT, Munich (DE); Siemens Medical Solutions USA, Inc., Malvern, PA (US)

(72) Inventors: Katharine Lynn Rowley Grant, Rochester, MN (US); Bernhard Schmidt, Fuerth (DE)

(73) Assignees: SIEMENS AKTIENGESELLSCHAFT, Munich (DE); SIEMENS MEDICAL SOLUTIONS USA INC., Malvern, PA (US)

(*) Notice: Subject to any disclaimer, the term of this patent is extended or adjusted under 35 U.S.C. 154(b) by 105 days.

(21) Appl. No.: 14/132,072

(22) Filed: Dec. 18, 2013

(65) Prior Publication Data
US 2015/0164454 A1 Jun. 18, 2015

(51) Int. Cl.
A61B 6/00 (2006.01)
A61B 6/03 (2006.01)

(52) U.S. Cl.
CPC ............. *A61B 6/505* (2013.01); *A61B 6/032* (2013.01); *A61B 6/482* (2013.01); *A61B 6/5217* (2013.01)

(58) Field of Classification Search
CPC ........ A61B 6/032; A61B 6/482; A61B 6/505; G01N 23/046
See application file for complete search history.

(56) References Cited

U.S. PATENT DOCUMENTS

| | | | |
|---|---|---|---|
| 5,852,647 A | 12/1998 | Schick et al. | |
| 7,046,834 B2 * | 5/2006 | Lee et al. | 382/132 |
| 2010/0135564 A1 | 6/2010 | Thomsen et al. | |
| 2010/0234719 A1 * | 9/2010 | Kelly et al. | 600/407 |
| 2013/0121465 A1 | 5/2013 | Cho | |

FOREIGN PATENT DOCUMENTS

| | | | |
|---|---|---|---|
| EP | 2583625 A1 | 4/2013 | |
| JP | H04263842 A | 9/1992 | |

\* cited by examiner

*Primary Examiner* — Courtney Thomas
(74) *Attorney, Agent, or Firm* — Harness, Dickey & Pierce, P.L.C.

(57) ABSTRACT

A method and a computing unit are disclosed for measuring and displaying the bone density of a patient. In at least one embodiment, separate projection data are used from a CT scan with at least two different x-ray energy regions; volume displays for bone material and at least one further material composition are generated; two DEXA projection recordings with different x-ray energy spectra are simulated from these volume displays; the two simulated DEXA projection recordings are used to determine the specific bone mass density according to the DEXA method; and at least one projection recording and at least one average specific bone mass density are output.

22 Claims, 4 Drawing Sheets

DEXA-P$_{EH}$      DEXA-P$_{EL}$

| A | B (g/cm²) | C (%) | T-value | D (%) | Z-value |
|---|---|---|---|---|---|
| L1 | 1,203 | 106 | 0,6 | 105 | 0,4 |
| L2 | 1,355 | 113 | 1,3 | 111 | 1,1 |
| L3 | 1,381 | 115 | 1,5 | 113 | 1,3 |
| L4 | 1,228 | 102 | 0,2 | 101 | 0,1 |
| L1-L2 | 1,277 | 110 | 0,9 | 108 | 0,8 |
| L1-L3 | 1,315 | 112 | 1,2 | 111 | 1,0 |
| L1-L4 | 1,289 | 109 | 0,9 | 108 | 0,7 |
| L2-L3 | 1,369 | 114 | 1,4 | 112 | 1,2 |
| L2-L4 | 1,315 | 110 | 1,0 | 108 | 0,8 |
| L3-L4 | 1,299 | 108 | 0,8 | 107 | 0,7 |

| A | B (g/cm²) | C (%) | T-value | D (%) | Z-value |
|---|---|---|---|---|---|
| Neck | 0,993 | 101 | 0,1 | 103 | 0,2 |
| Wards | 0,854 | 94 | -0,4 | 99 | -0,1 |
| Troch | 0,777 | 98 | -0,1 | 97 | -0,2 |
| Diaphysis | 1,163 | - | - | - | - |
| Overall | 0,985 | 98 | -0,1 | 99 | -0,1 |

| A | B (g/cm²) | C (%) | T-value | D (%) | Z-value |
|---|---|---|---|---|---|
| Neck | 1,002 | 102 | 0,2 | 104 | 0,3 |
| Wards | 0,839 | 92 | -0,5 | 97 | -0,2 |
| Troch | 0,816 | 103 | 0,2 | 101 | 0,1 |
| Diaphysis | 1,160 | - | - | - | - |
| Overall | 0,998 | 100 | 0,0 | 100 | 0,0 |

METHOD AND COMPUTING UNIT FOR MEASURING AND DISPLAYING THE BONE DENSITY OF A PATIENT

FIELD

At least one embodiment of the invention generally relates to a method for determining bone density with the aid of a CT system, wherein on the basis of a dual energy scan, a material breakdown into bone material and at least one further material composition is executed in order to display the bone density in a predetermined region of a bone.

BACKGROUND

In order to determine the bone density of a patient, there are currently two serious methods in the prior art. On the one hand dual energy x-ray absoptiometry (DEXA or DXA), on the other hand quantitative computed tomography (QCT).

With DEXA, two projective recordings of a patient are created using different x-ray energy spectra. On account of the different energy-specific absorption values for bone mineral and soft tissue, the portion of soft tissue can be subtracted and the proportion of the surface occupied by bone material can be determined. Measured values in $g/cm^2$ bone material are obtained as the result.

By using the two DEXA projection recordings with different x-ray energy spectra, a material breakdown into three material compositions can also be performed so that a rough composition of the entire body can be determined. Fat mass, fat-free mass without bones and bone mass are generally determined here as material compositions.

During the QCT, projections are recorded of a patient from a plurality of projection directions with an x-ray source rotating about the patient, the projections presenting two different x-ray spectra. Two volume image data records of different x-ray energy spectra are reconstructed with these projections. A material breakdown can in turn be executed with these two volume image data records, so that a volume recording is available at the end which exclusively represents the existing bone material in a 3D representation. It is thus possible to determine the actual mass density of bone mineral in the bone and to specify the bone density as a specific density in $kg/cm^3$.

The problem now is that the values determined in the DEXA and QCT for the bone density and also the recordings generated in each instance during these examinations are not directly comparable.

SUMMARY

At least one embodiment of the invention is directed to a method, a computing unit and/or a CT system, with which measuring results comparable with a DEXA examination are generated by a QCT examination.

Advantageous developments of the invention are the subject matter of subordinate claims.

Accordingly, in at least one embodiment, the inventors propose a method for measuring and displaying the bone density of a patient, the method comprising:

Use of a CT scan of the patient with at least two different x-ray energy regions, so that separate projection data exist for each x-ray energy region, Generation of volume displays for bone material and at least one further material composition, Calculation of two simulated DEXA projection recordings with a different x-ray energy spectrum in each instance using the volume displays for bone material and the at least one further material composition, Use of the two simulated DEXA projection recordings to determine the specific bone mass occupancy according to the DEXA method, Generation and output of at least one projection recording using at least one of the simulated DEXA projection recordings and at least one average, specific bone mass occupancy in at least one predetermined region of the at least one projection recording.

According to the further aspect of at least one embodiment of the invention, whereby the results of the CT examination are used directly to determine the bone density, the inventors also propose a method for measuring and displaying the bone density of a patient, the method comprising:

Use of a CT scan of the patient with at least two different x-ray energy regions, so that separate projection data exist for each x-ray energy region, Generation of volume displays for bone material and at least one further material composition, Calculation of a projection of the bone material occupancy of at least one section of the volume display of the bone density on a two-dimensional plane, Determination of the average bone material occupancy in at least one predetermined region of the projection, Output of the projection of the bone density and output of the bone material occupancy in the at least one predetermined region of the projection.

Aside from the afore-cited method, in at least one embodiment the inventors also propose a computing unit with a memory for storing at least one computer program, which is executed during operation, wherein the at least one computer program is to execute the afore-described method of an embodiment. This computing unit is preferably used in direct connection with a CT system.

BRIEF DESCRIPTION OF THE DRAWINGS

The invention is described in more detail below with reference to the figures, with only the features required to understand embodiments of the invention being shown. The following reference signs are used: 1: dual energy CT system; 2: first x-ray tube; 3: first detector; 4: second x-ray tube; 5: second detector; 6: gantry housing; 7: patient; 8: patient couch; 9: system axis; 10: computing unit; DE-CTE1, DE-CTE2: dual energy CT image data; DEXA: DEXA work flow; DEXA-PEL: DEXA projection data with a low x-ray energy spectrum; DEXA-PEH: DEXA projection data with a high x-ray energy spectrum; E1, E2, EL, EH: x-ray energy spectra; MZ: material breakdown; SIM: simulation of the DEXA projection; 3DK: volume display for bone material; 3DF: volume display for fat; 3DW: Volume display for soft tissue, in which in detail.

DETAILED DESCRIPTION OF THE EXAMPLE EMBODIMENTS

Figure 1:
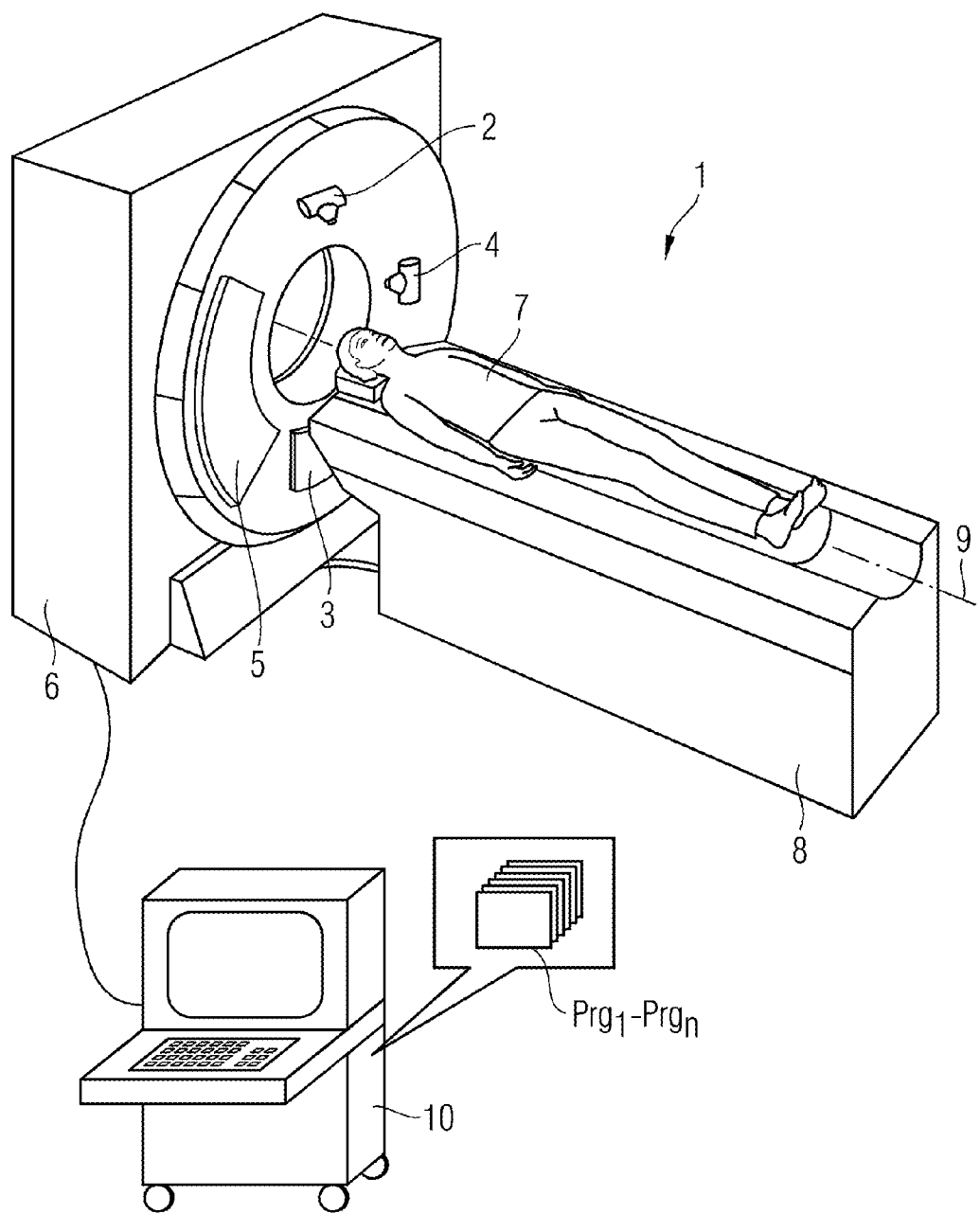
FIG. 1: shows a dual energy CT system for implementing an embodiment of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

DEXA methods and the bone density values determined by them have now developed in the field of medicine as gold standard despite their larger failure rate, since an examination ac-cording to this method is more cost-effective and less radiation-intensive for the patient than a CT examination. If however a CT examination has to be implemented for other medical reasons, the additional radiation exposure caused by an additional DEXA examination could be eliminated if values comparable to DEXA methods could be determined by the CT examination.

The inventors have identified that this can be achieved by a material breakdown into bone material and at least one further material composition being performed with a dual energy CT examination, and on the basis of the thus obtained volume image data for the at least two material compositions, the image generation of a DEXA examination being simulated. Based on the volume data known by the CT examination and the energy-specific absorption properties corresponding thereto, two projective x-ray recordings are therefore simulated with different x-ray energy spectra which are typical of DEXA methods. These simulated recordings can then be transferred to the known processing process of the DEXA methods, so that typical measuring results of the DEXA method are output at the end. The routinely known findings documentation known from the DEXA examination is then available to the treating physician. Accordingly, there is therefore also a direct comparability between the examination results, irrespective of whether they originate from a DEXA examination or a CT examination.

While assumptions in respect of the volumetric distribution of fat and soft tissue are made in the DEXA method, which are then incorporated into the evaluation of the image data, correction factors actually now of relevance can be used on account of the volumetric image data comprising the material breakdown of the CT image data which is now actually present to improve the calculations according to the DEXA method.

According to a second aspect of at least one embodiment of the invention, the inventors nevertheless also propose eliminating the path using the DEXA examination calculation method and calculating a projection, preferably in the ap-direction, directly from the volumetric CT image data and CT image data displaced prior to this according to material compositions and directly from the volumetric CT image data of the bone material and herefrom determining and outputting bone density values in the form of a mass occupancy of the bone material in $g/cm^2$.

Accordingly, in at least one embodiment, the inventors propose a method for measuring and displaying the bone density of a patient, the method comprising:

Use of a CT scan of the patient with at least two different x-ray energy regions, so that separate projection data exist for each x-ray energy region, Generation of volume displays for bone material and at least one further material composition, Calculation of two simulated DEXA projection recordings with a different x-ray energy spectrum in each instance using the volume displays for bone material and the at least one further material composition, Use of the two simulated DEXA projection recordings to determine the specific bone mass occupancy according to the DEXA method, Generation and output of at least one projection recording using at least one of the simulated DEXA projection recordings and at least one average, specific bone mass occupancy in at least one predetermined region of the at least one projection recording.

A mixture of fat and soft tissue or alternatively on the one hand fat and on the other hand soft tissue can advantageously be used as at least one further material composition.

It is further proposed, when determining the specific bone mass occupancy according to the DEXA method, to use a correction factor, which takes the mass ratio of fat and/or soft tissue to bones into account. It is particularly favorable here if the mass ratio of fat and/or soft tissue to bones is determined with the aid of the actual mass ratio found with material breakdown during the CT scan.

At least one x-ray spectrum, which differs from each of the x-ray spectra used for the simulated DEXA method, can basically be used for CT scan. If the x-ray spectra of the CT examination and the x-ray spectra of the simulated DEXA examination differ, the absorption coefficients used for the simulated DEXA method must be recalculated on the basis of the knowledge about the used material compositions in order to determine the developing absorption with the simulated DEXA method.

Alternatively, identical x-ray spectra can be used for the CT scan and simulated DEXA methods, so that the absorption coefficients of the material compositions used in the material breakdown of the CT can also be used directly for the simulation of the DEXA recordings.

According to the further aspect of at least one embodiment of the invention, whereby the results of the CT examination are used directly to determine the bone density, the inventors also propose a method for measuring and displaying the bone density of a patient, the method comprising:

Use of a CT scan of the patient with at least two different x-ray energy regions, so that separate projection data exist for each x-ray energy region, Generation of volume displays for bone material and at least one further material composition, Calculation of a projection of the bone material occupancy of at least one section of the volume display of the bone density on a two-dimensional plane, Determination of the average bone material occupancy in at least one predetermined region of the projection, Output of the projection of the bone density and output of the bone material occupancy in the at least one predetermined region of the projection.

In this connection, the detour of using the workflow of a DEXA method with previously simulated DEXA recordings on the basis of tomographic CT image data records broken down into material compositions is therefore avoided, but the volumetric material distribution of bone material from a CT examination is instead used, in order to generate a projective image data record, in which the surface occupancy of bone material, preferably in g/cm² is directly reproduced. Accordingly, an average mass occupancy of bone material can be determined and specified directly from this image data record for predetermined bone regions.

In order to achieve as similar an optical display with respect to the known findings output of the DEXA methods as possible, an x-ray projection can be simulated in the output projection in sub regions without bone occupancy, said x-ray projection displaying the projected volume display of the at least one further material composition. A projective recording generated in this way thus corresponds to the displays which are customary in DEXA methods.

In order to determine the volumetric distribution of the material compositions, in particular to generate volume displays for bone material and at least one further material composition, known material breakdown methods can be executed.

The process of the material breakdown itself can be executed here both on projection data and also on the previously reconstructed image data.

Aside from the afore-cited method, in at least one embodiment the inventors also propose a computing unit with a memory for storing at least one computer program, which is executed during operation, wherein the at least one computer program is to execute the afore-described method of an embodiment. This computing unit is preferably used in direct connection with a CT system.

FIG. 1 shows a schematic representation of a dual energy CT system 1 with a gantry housing 6, in which two rotatable emitter-detector combinations arranged on a gantry are disposed. The first emitter-detector combination includes the x-ray tube 2 and the opposing detector 3. The second emitter-detector combination is disposed in a rotational fashion likewise offset by 90° on the gantry and consists of the x-ray tube 4 and the opposing detector 5. In order to implement the dual energy scan, the patient 7 is scanned continuously or sequentially with the rotation of the gantry with the displaceable patient couch 8 along the system axis 9 through the radiation path of the two emitter-detector combinations 2, 3; 4, 5 and is at the same time scanned with two different x-ray energy spectra.

Based on the knowledge of the energy-specific absorption behavior of bone material and further material compositions, such as fat and soft tissue, a material breakdown of the reconstructible tomographic CT representations can be obtained in a known manner with the thus determined CT data so that a volumetric material distribution can be produced from material compositions with known energy-specific absorption properties. This is executed for instance in the computing unit 10, in which correspondingly suitable computer programs Prg1 to Prgn are stored.

Figure 2:
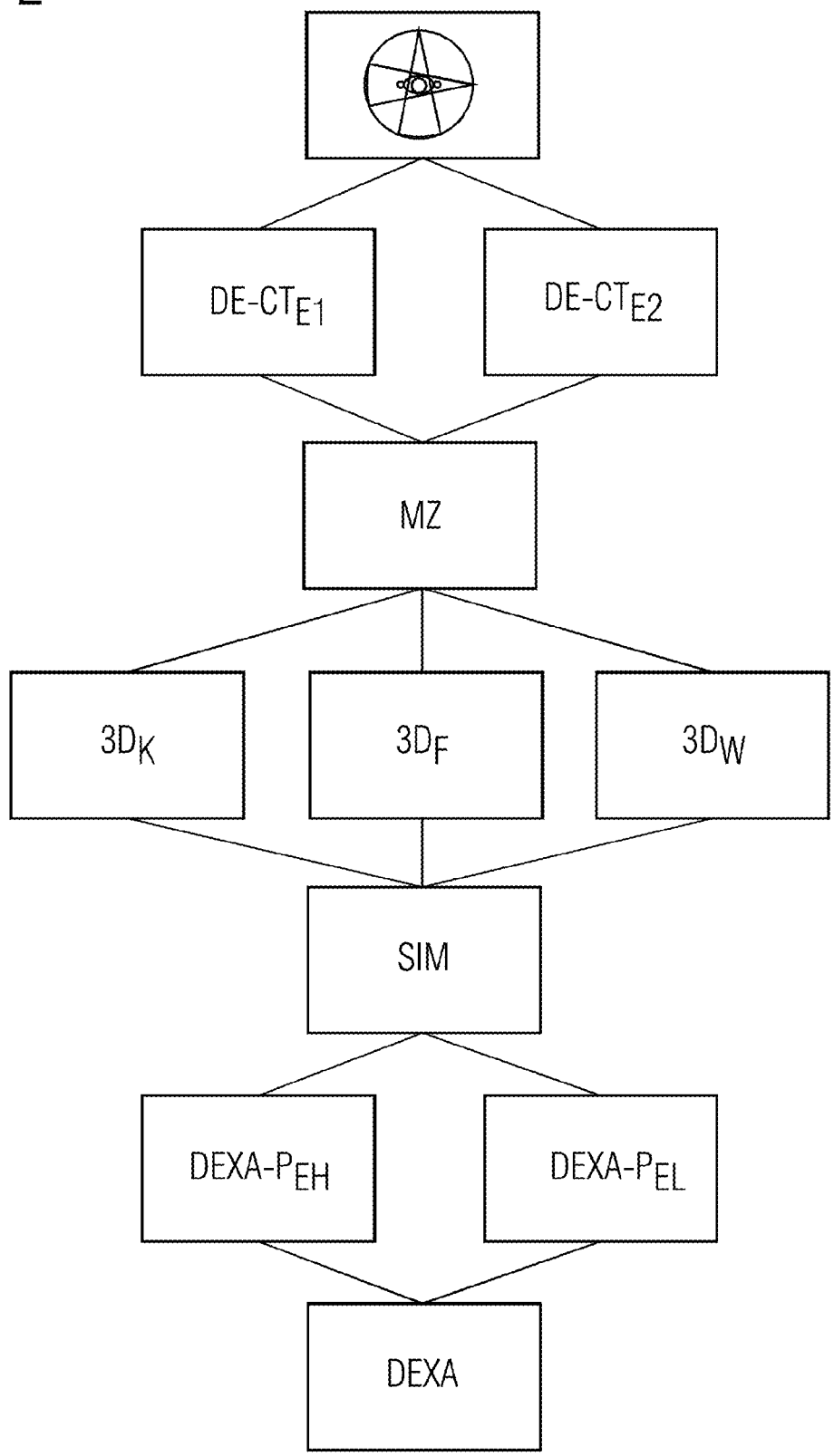
FIG. 2: shows a schematic diagram of a dual energy CT scan with DEXA evaluation.
Figure 3:
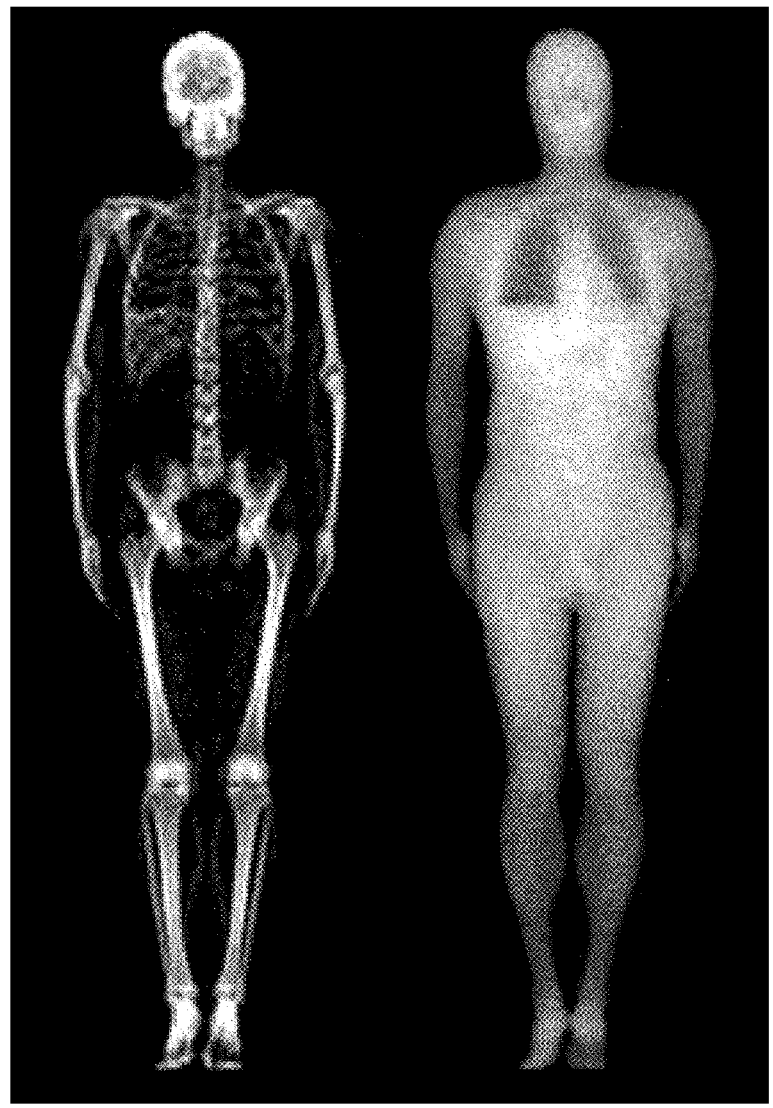
FIG. 3: shows DEXA projections simulated from CT image data with a high and low x-ray energy spectrum.

An example flow chart of an embodiment of the inventive method is shown in FIG. 2. The dual energy CT scan is shown symbolically in the topmost method step. This thus produces the two sets of dual energy CT image data DE-CTE1 and DE-CTE2 from the two different x-ray energy spectra E1 and E2. In accordance with an embodiment of the invention, a material breakdown MZ takes place with this CT image data, which, as a result, outputs the three-dimensional material distribution of the material compositions used, here 3DK, 3DF and 3DW for bones, fat and soft tissue. If these spatial distributions of the material compositions with their energy-dependent absorption coefficients are now known, the x-ray recording of two DEXA projections is simulated in the method step SIM and the DEXA projections DEXA-PEL and DEXA-PEH, are produced, wherein the indices L and H refer in each instance to the low energy x-ray energy spectrum EL and the high energy x-ray energy spectrum EH respectively. For an illustrative overview, two DEXA projections simulated by way of example, DEXA-PEL and DEXA-PEH are shown in FIG. 3.

The thus obtained simulated DEXA projection recordings DEXA-PEL and DEXA-PEH can now be used for the generally known DEXA workflow DEXA so that the familiar measured values of a DEXA method are available to the physician both in the illustrative display and also in the value output with bone density specifications in the form of an average surface occupancy for predefined bone regions. This method also achieves a direct comparison of original DEXA findings data and findings data relating to a dual energy CT examination. In addition to the DEXA findings data with mass occupancy values, the corresponding CT findings data can advantageously also be specified so that the investigating physician likewise has the values based on a more accurate measuring and calculation method available to him for control purposes and has if necessary also become used to this evaluation.

Figure 4:
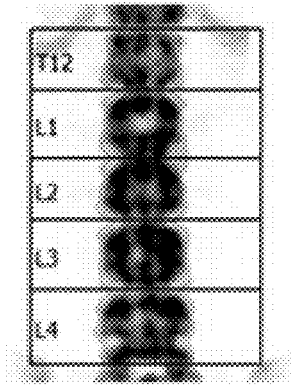
FIG. 4: shows a display of a DEXA measured value output on the basis of the DEXA projections from FIG. 3.
Figure 4:
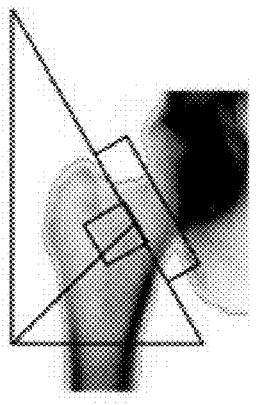
Figure 4:
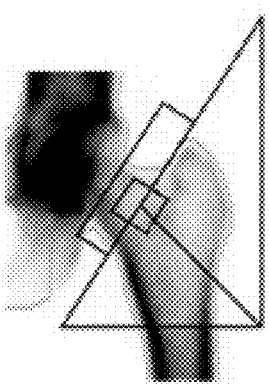

An example measured value output of the simulated DEXA examination using dual energy CT image data is shown in FIG. 4. Here, as is generally the case, the left side of the figure shows detailed extracts of DEXA projections of a spinal column, the right femur and the left femur. The examined regions are shown to the right of this in column A and the determined average surface occupancies of the regions are specified in g/cm² in column B. Details relating to the T-values and the Z-values which are not relevant to the invention follow in the columns under C and D.

In order to determine the T-values, there are various methods and devices, which cannot be compared with one another. For this reason no absolute density or surface density is generally specified in the findings, instead, the deviations from the normal are specified in multiples of a standard deviation, as so-called T-value (t-score) in the form of a dimensionless variable. According to the valid definition of the WHO, osteoporosis is present if the measured value of the bone density measurement lies at least 2.5 standard deviations below the average of the gender-identical 30 year old healthy person (peak bone mass), i.e. a T-value≤−2.5 is present. Standard deviations between −1 and −2.5 refer to osteopenia.

The specification of the T-value with reference to the "peak bone mass" is problematic in that a growing proportion of the population with increasing age would be seen as being "ill", in the case of 70-year old women, this would be almost 50% of the examined patients. A value is therefore additionally specified, which relates to healthy men and women of the same age and same ethnicity, the Z-value. A normal Z-value of greater than −1 indicates that the bone density is typical of age. Age is not an illness and can also not be treated. In the case of very old people, an increased risk of fracture is also typical of age. With a low T-value but a normal Z-value, osteologists therefore advise against medical therapies and recommend preventive measures such as gymnastics, abandoning sedatives, reducing tripping hazards in the home, suitable visual and walking aids.

Overall, an embodiment of the invention therefore proposes, on the basis of a dual energy CT scan, to determine the material distribution by paying particular attention to the bone mineral in the body of a patient, to determine therefrom the absorption values for a simulated DEXA scan, to simulate two DEXA projections with a high and low x-ray energy spectrum and to evaluate these two DEXA projections with the known DEXA workflow so that the usual findings parameters of a DEXA examination are output as the result. Alternatively, it is also proposed to determine the spatial distribution of the bone mineral on the basis of the afore-described CT scan by material breakdown and to project the same onto a plane so that the mass occupancy of the bone mineral which is typical of the DEXA examination can be output.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred example embodiment, the invention is not limited by the disclosed examples and other variations can be derived herefrom by the person skilled in the art, without departing from the scope of protection of the invention.

The invention claimed is:

1. A method, comprising:
using a CT scan of a patient with at least two different x-ray energy regions, so that separate projection data exist for each x-ray energy region;
generating volume displays for bone material and at least one further material composition;
calculating two simulated dual energy x-ray absorptiometry (DEXA) projection recordings, each with a respectively different x-ray energy spectrum, using the volume displays for bone material and the at least one further material composition;
using the two simulated DEXA projection recordings to determine a specific bone mass occupancy; and
generating and outputting at least one projection recording using at least one of the simulated DEXA projection recordings and at least one average, specific bone mass occupancy in at least one region of the at least one projection recording.

2. The method of claim 1, wherein a mixture of fat and soft tissue is used as at least one further material composition.

3. The method of claim 1, wherein, either fat or soft tissue is used as an at least one further material composition.

4. The method of claim 1, wherein, with the determination of the specific bone mass occupancy, a correction factor is used, which takes a mass ratio of at least one of fat and soft tissue relative to bones into account.

5. The method of claim 4, wherein the correction factor, which takes the mass ratio of at least one of fat and soft tissue relative to bones into account, is determined with the aid of an actual mass ratio found with a material breakdown during the CT scan.

6. The method of claim 1, wherein at least one x-ray spectrum is used for CT scan, which differs from each x-ray spectrum used for the two simulated DEXA projection recordings.

7. The method of claim 1, wherein identical x-ray spectra are used for the CT scan and the two simulated DEXA projection recordings.

8. The method of claim 1, wherein volume displays for bone material and at least one further material composition are generated using a material breakdown method.

9. The method of claim 8, wherein the material breakdown is executed on projection data.

10. The method of claim 8, wherein the material breakdown is executed on reconstructed CT image data.

11. The method of claim 1, wherein corresponding material occupancy values and material density values are output at the same time.

12. A computing unit, comprising:
a memory, configured to store at least one computer program, which is executed during operation of the computing unit, the at least one computer program, when executed, performing the method of claim 1.

13. A CT system, comprising:
the computing unit of claim 12.

14. A computer readable medium including program segments for, when executed on a computer device, causing the computer device to implement the method of claim 1.

15. A method, comprising:
using a CT scan of a patient with at least two different x-ray energy regions so that separate projection data exist for each of the x-ray energy regions;
generating volume displays for bone material and at least one further material composition;
calculating a projection of bone material occupancy of at least one section of the volume display of the bone density on a two-dimensional plane;
determining an average bone material occupancy in at least one region of the projection; and
outputting the projection of the bone density and outputting the bone material occupancy in the at least one region of the projection.

16. The method of claim 15, wherein an x-ray projection is simulated in the output projection in sub areas without bone occupancy, which displays the projected volume display of the at least one further material compensation.

17. A computing unit, comprising:
a memory, configured to store at least one computer program, executable during operation of the computing unit, the at least one computer program, when executed, performing the method of claim 15.

18. A CT system, comprising:
the computing unit of claim 17.

19. A computer readable medium including program segments for, when executed on a computer device, causing the computer device to implement the method of claim 15.

20. The method of claim 15, wherein volume displays for bone material and at least one further material composition are generated using a material breakdown method.

21. The method of claim 20, wherein the material breakdown is executed on projection data.

22. The method of claim 20, wherein the material breakdown is executed on reconstructed CT image data.

* * * * *